United States Patent [19]

Wilkes

[11] 4,366,333

[45] Dec. 28, 1982

[54] PROCESS OF PROLONGING THE LIFE OF ESTER HYDROGENATION CATALYST

[75] Inventor: John B. Wilkes, Richmond, Calif.

[73] Assignee: Chevron Research Company, San Francisco, Calif.

[21] Appl. No.: 132,916

[22] Filed: Mar. 24, 1980

Related U.S. Application Data

[63] Continuation-in-part of Ser. No. 52,515, Jun. 27, 1979, abandoned.

[51] Int. Cl.³ .................................................. C07C 31/20
[52] U.S. Cl. .................................................... 568/864
[58] Field of Search ........................................ 568/864

[56] References Cited

U.S. PATENT DOCUMENTS 2,285,448  6/1942  Loder .................................. 568/864
4,087,470  5/1978  Suzuki ............................... 568/864

Primary Examiner—Joseph E. Evans
Attorney, Agent, or Firm—D. A. Newell; T. G. De Jonghe; C. J. Caroli

[57] ABSTRACT

The life of the hydrogenation catalyst in reducing a mixture of glycolate ester to ethylene glycol can be extended by lowering the polyglycolide ester content of the mixture by transesterification, that is, heating in the presence of alcohol, after which the resulting mixture is hydrogenated.

5 Claims, 1 Drawing Figure

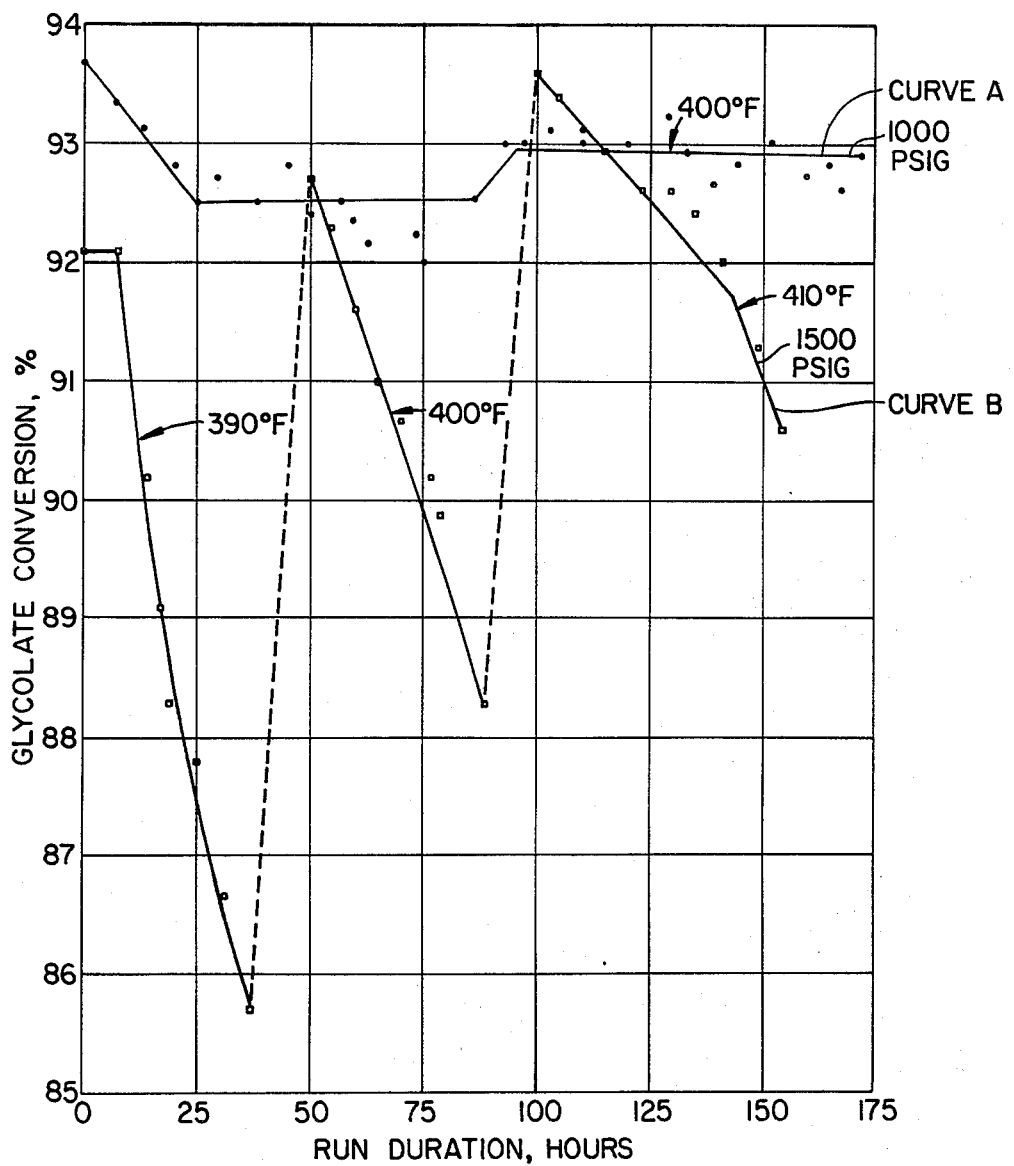
FIG._1.

PROCESS OF PROLONGING THE LIFE OF ESTER HYDROGENATION CATALYST

CROSS-REFERENCE TO RELATED APPLICATION

This application is a continuation-in-part of U.S. Ser. No. 52,515, filed June 27, 1979, now abandoned.

BACKGROUND OF THE INVENTION

The present invention relates to a process of prolonging the life of the hydrogenation catalyst used in the catalytic hydrogenation of glycolic acid esters to produce ethylene glycol.

Generally, the hydrogenation of esters to alcohols is well known, as can be seen, for example, from U.S. Pat. No. 1,605,093. According to this patent, a copper catalyst is used in the hydrogenation. Also, esters have been reduced to alcohols by using various means, such as lithium aluminum hydride or sodium plus an alcohol.

U.S. Pat. No. 2,285,448 granted June 9, 1942, discloses the liquid phase hydrogenation of the esters of glycolic acid to produce ethylene glycol. The liquid phase hydrogenation is carried out at pressures in excess of 100 atmospheres and preferably above 400 atmospheres with temperatures between 125° and 325° C. According to this patent, a copper-magnesium catalyst is preferred. It is stated in the patent at page 1, column 2, lines 47-52 that in place of magnesium oxide, other metal oxides may be employed to promote the activity of the copper oxide.

U.S. Pat. No. 2,305,104 is likewise concerned with the hydrogenation of alkyl glycolates. This patent relates to a vapor phase hydrogenation process using apparatus wherein catalyst degradation is reduced to a minimum. The process is carried out by reacting the alkyl ester of glycolic acid and hydrogen in a catalyst charged reaction zone and subsequently, mixing the gases issuing therefrom with sufficient additional hydrogen to maintain the reaction products in the vapor phase and to maintain the esters and hydrogenated products in the vapor phase, and reacting the resulting mixture in another catalyst charged reaction zone.

British Pat. No. 575,380 relates to a process of hydrogenating an ester of glycolic acid to produce ethylene glycol under conditions such as to minimize loss of catalyst activity. The process is carried out in the vapor phase, wherein the gaseous mixture containing hydrogen and between 1.5% and 8% by volume of the ester of glycolic acid is contacted with the hydrogenating catalyst at a pressure between 10 and 75 atmospheres and at a temperature between 150° and 300° C.

Commonly assigned U.S. Pat. Nos. 3,911,003 and 4,087,470 granted, respectively on Oct. 7, 1975 and May 2, 1978, the disclosures of which are herein incorporated by reference, are concerned with the preparation of glycolic acid and diglycolic acid and their reduction to ethylene glycol or diethylene glycol. The process disclosed in U.S. Pat. No. 4,087,470, involves the steps of (1) contacting formaldehyde, carbon monoxide and hydrogen in the presence of hydrogen fluoride to form glycolic and diglycolic acids; (2) contacting the acids of step (1) with ethylene glycol, diethylene glycol or mixtures thereof to produce ethylene glycol glycolate and diglycolate, diethylene glycol glycolate and diglycolate, or mixtures thereof; and (3) contacting the ester glycolate and diglycolate products of step (2) with hydrogen in the presence of a hydrogenation catalyst to produce the desired ethylene glycol or diethylene glycol.

In accordance with the aforesaid U.S. Pat. No. 4,087,470, the esters of step (2) above are prepared by first purifying the acid product of step (1) essentially by removal of the hydrogen fluoride catalyst. Pursuant to U.S. application Ser. No. 931,333, filed Aug. 7, 1978, HF is most effectively removed by heating to a temperature above about 130° C., preferably with gas or vapor stripping, such treatment resulting in the formation of a polymer of a glycolic acid.

Glycolic acid possesses characteristics of both a carboxylic acid and an alcohol and is accordingly capable of forming linear esters by reaction between a hydroxyl group of one molecule of glycolic acid and the carboxyl group of another molecule of glycolic acid, with the simultaneous formation of water. These esters are monoglycolide or polyglycolides and may be formed even in concentrated aqueous solution, as described in pages 632 and 633 of Vol. 10 of the second edition of Kirk-Othmer's "Encyclopedia of Chemical Technology."

Following dehydration, the anhydrous glycolic acid (i.e., the various dehydrated forms of glycolic acid, and in particular a mixture of glycolic acid and polyglycolides) as prepared, for example, in accordance with the aforesaid U.S. Pat. No. 4,087,470 is reacted with an alcohol under esterification reaction conditions to produce the glycolate esters, as shown, for example, in U.S. Pat. No. 2,331,094. Suitable alcohols are methanol, ethanol, n- and iso-propanol, n- and iso-butanol, octanol and higher straight and branched-chain alcohols, polyhydric alcohols, such as ethylene glycol and diethylene glycol, as well as the mixtures or particular fractions of the mixtures of alcohols obtained by the hydroformylation of olefins.

SUMMARY OF THE INVENTION

The invention is based on the discovery that the life of the hydrogenation catalyst used in the liquid phase hydrogenation of a mixture of esters obtained by reacting glycolic acid and polyglycolides with an alcohol and having a polyglycolide ester content of more than 22% by weight, based on total ester content of the mixture, can be prolonged if prior to the hydrogenation treatment said mixture is transesterified by heating it in the presence of at least a stoichoimetric amount of alcohol, based on the polyglycolide esters, until the content of the polyglycolide ester is reduced below about 22% of the total ester content.

DESCRIPTION OF THE FIGURE

FIG. 1 is a plot of the ester conversion to alcohol as a function of time at various temperatures and pressures comparing the practice of the present invention, as illustrated by Curve A [Example 2(b)] with prior art practice, as illustrated by Curve B [Example 1(b)].

Curve B shows that, in order to obtain an overall relatively high conversion, the temperature must be increased periodically. That is, at a given temperature, e.g., 390° F., conversion proceeds for a while, but then rapidly falls, until boosted by an increase in temperature to 400° F. At this point the conversion falls off until the temperature is again increased.

The maximum temperature for ester hydrogenation over a copper-containing catalyst is about 470° F. To maintain catalyst activity, as hereinabove indicated, the reaction temperature is periodically increased, and by this treatment the maximum temperature of 470° F. is reached after a relatively short reaction time. At this high temperature the catalyst is soon destroyed and must be replaced, with consequent increase in process costs.

Curve A, on the other hand, shows an average conversion rate of 92.7% can be maintained for a long period of time with very little, if any, reduction in activity by the practice of the present invention.

DETAILED DESCRIPTION OF THE INVENTION

When preparing the glycolic acid for esterification and subsequent hydrogenation to produce ethylene glycol, the glycolic acid, as previously noted, is advantageously dehydrated, as described, for example, in the aforementioned U.S. Pat. No. 4,087,470, by heating to a temperature in about the range 120°–200° C. under 0.1 to 0.2 atmospheric pressure. As a result, polyglycolides having the formula $H(OCH_2CO)_xOH$, wherein x is an integer of 2 to 4, are formed. These may be regarded as self-esters or homopolyesters of glycolic acid. The "anhydrous glycolic acid", by which, wherever the term is used herein, is meant a mixture of free glycolic acid, and the polyglycolides and other dehydration products of glycolic acid is esterified with an appropriate alcohol under conditions effective to produce in turn a mixture of glycolate and polyglycolate esters. In preparing the ester product for hydrogenation it is desirable to achieve at least 98% esterification of all acid groups, as measured by comparing the acid number (ASTM D 2086) with the saponification number [Example 1(a)]. According to U.S. Pat. No. 4,087,470, hereinbefore mentioned, essentially complete esterification is achieved by adding hot ethylene or diethylene glycol and removing water formed during esterification until substantially all the carboxyl groups of the anhydrous acid are esterified. Suitable conditions for esterification include a temperature of from about 300° F. to 480° F., preferably from about 340° F. to about 430° F., and a pressure from about 0.1 psia to about 100 psia, preferably from about 5 psia to about 50 psia. Further, in carrying out the esterification reaction it is desirable to use an excess of alcohol. Suitable mol ratios of glycol to acid during esterification vary from about 1.5:1 to about 10:1, preferably from about 2:1 to about 6:1.

The product resulting from the esterification of a mixture of free glycolic acid and polyglycolides in the anhydrous glycolic acid will generally comprise esterified glycolic acid and from about 20% to 50% of esterified polyglycolide, based on total ester content. The polyglycolide esters may be represented by the formula $H(OCH_2CO)_xOR$, wherein X is an integer of 2 to 4, and R is an alkyl group of 1 to 10 carbon atoms, a hydroxylalkyl of 2 to 6 carbon atoms, an alkoxyalkyl of 3 to 6 carbon atoms, or a hydroxyalkoxyalkyl of 4 to 8 carbon atoms, the R group being derived from the alcohol of esterification. Such a mixture forms the feedstock for the hydrogenation treatment to produce ethylene glycol.

Now, in accordance with the invention, I have found that when such feedstock is used, the catalyst life of the hydrogenation catalyst can be extended by subjecting the ester mixture feedstock to a treatment which has the effect of reducing the esterified polyglycolide content below about 22% of the total ester as determined by gas chromatography, high pressure liquid chromatography or proton nuclear magnetic resonance spectroscopy. Determination of the content of esterified polyglycolide esters is usually most conveniently made by gas chromatography. Typically, the analysis is carried out using a column containing liquid methyl silicone polymer, such as that known as OV-101, on a finely divided support, and using a sensitive detector such as a flame ionization detector. The details of the analytical technique used will depend on the nature of the alcohol used for the esterification and transesterification. Usually it will be advantageous to use a relatively short gas-chromatographic column, about 90 to 150 cm long. If the alcohol used is relatively volatile and forms relatively volatile glycolic esters, such as methyl and isobutyl alcohols, the esters can be analyzed by gas chromatography without any prior treatment. Where the alcohols used for esterifying and transesterifying the polyglycolide are relatively non-volatile, such as ethylene glycol, diethylene glycol, and 2-ethyl-1-hexanol, it is preferable to acetylate the mixture before analysis to make the materials more volatile. Acetylation can be carried out without significantly affecting the polyglycolide content of the mixture by reacting at 70°–120° F. with an excess of acetic anhydride containing pyridine as an acetylation catalyst. The entire reaction mixture may then be analyzed by gas chromatography. Identification of the glycolic and polyglycolide ester peaks in the gas chromatograph can be made by comparison of molecular weights with retention times, and comparison with compounds of known composition in the usual manner.

The treatment of the feedstock is accomplished by heating the ester mixture in the presence of alcohol under transesterification conditions. The alcohol used may be the same as used in forming the ester mixture or it may be a different alcohol suitable for esterification in the first instance. The amount of alcohol used is at least a stoichiometric amount up to 1000 mol % excess, preferably from 250 to 400 mol % based on esterified polyglycolide when dihydric hydroxyalkyl or hydroxyalkoxyalkyl alcohols are used. The preferred amounts will be twice as much when monohydric alcohols are used. Temperatures suitable for the transesterification can vary from about 300°–525° F., preferably 375° F. to 445° F., over a period of time of from about 10 to 120 minutes, preferably 20 to 90 minutes.

The transesterified product as thus prepared is suitable for the hydrogenation treatment. The liquid phase hydrogenation can be conducted at temperatures from about 300° F. to about 570° F., preferably from about 355° F. to about 480° F., and pressures from about 300 psig to about 5,000 psig, preferably from about 600 psig to about 2,000 psig. Considerable latitude in the temperature and pressure of hydrogenation and of residence time is possible depending upon the use and choice of hydrogenation catalyst.

The hydrogenation catalyst is one containing copper which is well-dispersed and stabilized against sintering. (G. Natta and R. Rigamonti, "Handbuch der Katalyse," Vol. 5, pages 567–584, G. M. Schwab, Editor; Springer Verlag, Vienna, 1957).

Copper catalysts can be supported on, or copper compounds can be co-precipitated with, a wide variety of materials such as kieselguhr, alumina, magnesium silicate, and the oxides of Ce, Th, Cr, U, Mn, Zn, Fe, Si, Be, Ba, Sr, Ti, Zr, and V. Copper-chromia or copper chromite catalysts, often modified by the addition of BaO, CaO, and $MnO_2$, NaOH, iron oxides and phosphates has been widely used for the hydrogenation of esters to alcohols. While most of the modifying materials probably function mainly to disperse the copper hydrogenation component and to stabilize it against sintering, some of the components of the mixed catalysts, such as ZnO, Fe, and $Cr_2O_3$ may have some catalytic properties of their own. Other catalytically active materials such as Ni, Co, W, Mo, Ag, Cd, Sn, Fe and platinum group metals may be added in certain cases. Some components, such as BaO and ZnO, may also function to protect the copper catalyst against poisons in the feeds by reacting the catalyst poisons such as sulfur compounds. As especially suitable catalyst for the hydrogenation of glycolic esters to ethylene glycol is one made from the oxide, hydroxide or carbonate forms of cobalt, zinc and copper a described in U.S. Pat. No. 4,113,662, the disclosure of which is herein incorporated by reference.

The advantages of the invention are particularly applicable to a hydrogenation process effected using the catalyst composition of my copending U.S. application Ser. No. 881,084 filed Feb. 24, 1978, now U.S. Pat. No. 4,199,479, the disclosure of which is hereby incorporated by reference. According to this application an effective hydrogenation catalyst is a copper hydrogenation catalyst comprising from about 1 to about 30 weight percent of finely divided silica in combination with from about 70 to about 99 weight percent of a select hydrogenation component comprising copper in elemental or compound form and zinc oxides.

The catalyst may be extruded, tableted, or used as a powder depending upon the contemplated use, for example, as in fixed bed, fluid bed, or slurry reaction usage. Broadly, the more useful catalyst for fixed bed operation will be sized in the diameter range from about 05 mm to 15 mm, preferably 1 to 5 mm.

Usually it is preferable to reduce most or all of the readily reducible copper components in the catalyst to metallic copper before addition of the ester feed to the catalyst. The conditions of reduction are chosen to avoid temperature rises that will produce thermal sintering, for example as described by J. S. Campbell, [Preprints of the Petroleum Division, American Chemical Society, Vol. 14, No. 3, pages A129–A141 (September 1969)]. Reduction of the catalyst can be carried out after the addition of the ester feed. However, reduction of the copper components of the catalyst by this technique is usually less complete and less easily controlled.

The following examples illustrate the practice of the invention, but are not to be construed as limiting the invention thereto since many variations will occur to those skilled in the art.

In the Examples, the apparatus for carrying out the hydrogenation reaction comprised a stainless steel tube reactor 5 mm in internal diameter and 32 cm long, placed in a large block of aluminum bronze slotted to fit the reactor. This block was equipped with means to maintain and measure the desired reaction temperature. The reactor was also provided with inlet means for feeding uniform flows of hydrogen and of liquid ester feed at the desired pressure and with outlet means for the reaction products. Conventional apparatus for separating the gas from the liquid product and for recovering the desired ethylene glycol was also provided.

EXAMPLE 1

(a) An aqueous solution of purified glycolic acid containing 424 g. (5.58 mols) of glycolic acid in 633 g. of solution was partially dehydrated by distilling off the water of solution under a vacuum of 100 torr until the temperature of the liquid reached 300° F. While still hot, 1350 g. (12.72 mols) of diethylene glycol was added. The esterification was completed by heating the solution and distilling off the liberated water through a distillation column at 200 torr until no significant amount of additional water was formed and diethylene glycol was distilled overhead. The distillation pot temperature rose to 390° C.–400° F. This entire process was repeated 5 times and the batches of ester were combined. A sample of the combined ester solution was saponified by refluxing for 15–20 minutes with a solution of about 1.5 N in NaOH (prepared by dissolving 50% aqueous sodium hydroxide solution in diethylene glycol) and was found to have a saponification number of 202.3, as calculated by the method of ASTM D 1387. This corresponds to 59.2% diethylene glycol glycolate, calculated on the assumption that all of the glycolic moieties are present as the monomeric diethylene glycol ester. Analyses of the ester by acetylation and gas chromatography showed that 59.3% of the ester was monomeric and 40.7% polyglycolide esters. In the polyglycolide ester fraction, 80.9% of the ester had two glycolic acid moieties esterified with one diethylene glycol molecule, and 19.1% of the ester had three glycolic acid moieties esterified with one diethylene glycol molecule.

(b) To the hydrogenation apparatus there was charged a mixture comprising 2.5 cc of hydrogenation catalyst, and 5.0 cc of alpha-alumina. The hydrogenation catalyst was prepared in accordance with application Ser. No. 881,844, hereinabove mentioned, and was an intimate mixture of 2/1 molar ratios of copper and zinc oxide with 11.9% silica, by weight. The hydrogenation catalyst was pelleted to give pellets 4.76 mm in diameter and then crushed and screened before use to pass through a 14-mesh Tyler screen and be retained on a 28-mesh Tyler screen. This gave granules about 0.6–1.2 mm in size, which had a BET [S. Brunauer, P. H. Emmett, and E. Teller, JACS; Vol. 60, page 309 (1938)] surface area of 84 $m^2$/gram and a pore volume of 0.28 ml/gram. The catalyst was reduced by passing a mixture of 20 volume % hydrogen in nitrogen at atmospheric pressure through the catalyst bed while gradually raising the temperature from 200° F. to 400° F. Hydrogenation was accomplished by passing an excess of hydrogen through the catalyst bed at a pressure from 1,000 to 1,500 psig, along with liquid ester at different temperatures, feed rates, etc. to test catalyst activity, selectivity and stability. When the ester feed mixture described in (a) was passed through the catalyst bed at 16 ml/hour, a pressure of 1,500 psig, and a temperature of 390° F., a conversion of 92.1% of the ester was observed. The conversion dropped throughout the run period, to 85.7% after 40 hours of operation at these conditions. The rate of loss of conversion in this time period was 16% per 100 hours of operation. At this point the temperature was increased to 400° F. The conversion increased to 92.7%, but after 38 additional hours of operation, the conversion had decreased to 88.3%, a rate of loss of over 11% conversion per 100 hours. Further increase of the temperature to 410° F. increased conversion to 93.6%, but after operation for an additional 55 hours, conversion had decreased to 90.6%. The results are graphically shown in FIG. 1, Curve B.

The test was terminated because of unsatisfactory catalyst stability, as demonstrated by the data.

EXAMPLE 2

(a) A batch of diethylene glycol ester of glycolic acid was prepared as in (a) and was found to have a saponification number of 208.4 which corresponds to 61.0% diethylene glycol glycolate, calculated on the assumption that all of the glycolic moieties are present as monomeric diethylene glycol ester. Analysis of this ester by acetylation and gas chromatography showed that 66.0% was monomeric glycolic ester, 31.1% had two glycolic units esterified with one diethylene glycol unit, and 2.9% of the ester had three glycolic acid units esterified with one diethylene glycol molecule.

A portion of this ester product was mixed with an equal weight of fresh diethylene glycol, and heated to a temperature of 405°–410° F. at 200 torr for 75 minutes. During this time a small amount of water was distilled off. The saponification numer of the product was 104.1, which corresponds to 30.5% diethylene glycol glycolate, calculated on the assumption that all of the glycolic moieties are present as the monomeric diethylene glycol ester. The mol ratio in this material was 4.54 mols of diethylene glycol to one mol of glycolic acid. Analysis of the mixture by acetylation and gas chromatography showed the presence of 89.4% monomeric glycolic ester, and 10.6% of an ester having two glycolic acid units esterified with one diethylene glycol unit. No ester could be detected which had three glycolic acid units esterified with one diethylene glycol molecule.

(b) The hydrogenation reactor was charged with a 2.5 cc portion of the same pelleted, crushed and screened catalyst described in Example 1, mixed with 5 cc. of 28–35 mesh alpha-alumina. The catalyst was reduced in the manner described in Example 1. Hydrogenation of the diluted and depolymerized ester feed mixture described in Example 2a was conducted at 1,000 psig and 400° F. with the ester feed mixture fed at 16 ml/hour. After a short initial period the conversion of the glycolic ester by the hydrogenation stabilized at 92.7 conversion. After 150 hours of additional operation at these conditions, the conversion was still 92.7, as shown in FIG. 1, Curve A. The loss of catalyst activity with this diluted and transesterified feed was undetectable, in contrast to the activity losses of 11–16% conversion per 100 hours with the conventional glycolic ester feed of Example 1 containing high levels of polymeric glycolic esters.

EXAMPLE 3

A sample of anhydrous glycolic acid obtained from the dehydration of the acid product was made in a continuous operation in accordance with U.S. Pat. No. 3,911,003, namely, by contacting formaldehyde with carbon monoxide in the presence of hydrogen fluoride under conditions to produce glycolic acid and diglycolic acid. The anhydrous glycolic acid was esterified by using an excess of diethylene glycol as in Example 1. Transesterification was accomplished by further heating at 375° F.–410° F. for 3 hours after esterification was complete. The saponification number of the resulting ester solution was 101.5, which corresponds to 29.7% diethylene glycol glycolate, calculated on the assumption that all of the glycolic ester is in the monomeric form. The mol ratio of diethylene glycol moieties to glycolic acid moieties in the solution was 4.66/1.0. Analysis by acetylation and gas chromatography showed that over 89% of the ester was present as monomeric glycolic ester, 10.5% of the ester had two glycolic acid units esterified with one diethylene glycol unit, and that less than 0.2% of the ester had three glycolic acid units esterified with one diethylene glycol unit. The ester feed solution also contained some ester of diglycolic acid, and traces of other impurities such as sulfur compounds and metal ions.

The hydrogenation reactor was charged with 2.5 ml of 14 to 28 mesh pelleted and crushed catalyst, mixed with 2.5 ml of 28–35 mesh alpha-alumina particles. The catalyst had a 1:1:1 molar ratio of copper:cobalt:zinc, as the oxides, and contained 11.5 wt. % silica. The catalyst had a BET surface area of 149 m$^2$/gram, and a pore volume of 0.39 ml/gram. After reduction of the catalyst, 6 ml/hour of the ester feed was passed over the catalyst along with an excess of hydrogen. After the catalyst activity leveled out, the hydrogenation was tested at 400° F. and 990 psig. The initial conversion of the glycolic ester was 94.1%, and declined to 91.6% after 58 hours of operation. Subsequent testing at 420° F. and 1540 psig gave, initially, 92.2% conversion of the glycolic ester, which declined to 89.6% conversion after 106 additional hours of operation, for a loss of 2.5% conversion per 100 hours. The results obtained in accordance with this example, while acceptable, are not as good as those obtained in accordance with Example 2. The inferior results are attributable to the impurities in the ester feed solution hereinabove mentioned.

EXAMPLE 4

A feed of ethylene glycol glycolate was made by dehydrating an aqueous solution of highly purified glycolic acid, adding ethylene glycol, and esterifying at a temperature of about 385° F. The final product had a saponification number of 230.0, and an acid number of 0.96, which showed over 99.5% esterification. No additional time was allowed for transesterification of the polyglycolide esters. The saponification number corresponds to a concentration of 49.2% ethylene glycol glycolate, calculated on the assumption that all of the glycolic moieties are present as the monomeric ethylene glycol ester. This composition requires 3.0 mols of ethylene glycol per mol of glycolic acid moieties.

The hydrogenation reactor was charged with 5 ml of the 15 to 28 mesh crushed and screened Cu:Co:Zn oxides plus silica catalyst described in Example 3. After catalyst reduction, the purified feed was passed over the catalyst at the rate of 16 ml/hour with excess hydrogen. The catalyst lost activity rapidly. At 400° F. and 1,000 psig the glycolic ester conversion decreased from 87.5% to 84.6% in only 5 hours of operation. At 400° F. and 1,500 psig, the conversion decreased from 92.8% to 91.6% in 11 hours, or at a rate of loss of activity of 10.9% conversion per 100 hours. This rate of activity loss is much faster than than in Example 3, even though the feed for Example 3 contained some typical catalyst poisons. The feed for Example 4 was highly purified, except for the presence of polyglycolide esters.

EXAMPLE 5

The other portion of the diethylene glycol ester of glycolic acid prepared in Example 2(a) was hydrogenated without transesterification. In the hydrogenation step the catalyst employed was like that of Example 1, the temperature being 360° F. and the presence 1,500 psig. The activity loss of the catalyst was determined as in Example 1(b) and found to be 14% per 100 hours.

EXAMPLE 6

A procedure similar to Example 1(a) was followed to produce the diethylene glycol ester of glycolic acid. Saponification analysis as in Example 1(a) showed a diethylene glycol glycolate concentration of 56%. Analysis of the ester by acetylation and gas chromatography showed that 26% of the ester was polymeric. This product was diluted with an equal weight of diethylene glycol and then hydrogenated without transesterification. In the hydrogenation the catalyst was like that of Example 3, the temperature and pressure of hydrogenation being respectively 360° F. and 1,500 psig. The activity loss of the catalyst again was determined as in Example 1(b), and found to be 12% per 100 hours.

EXAMPLE 7

Esterification and transesterification were performed similar to Example 3 to produce the diethylene glycol ester to glycolic acid. Saponification analysis showed it to contain 39% diethylene glycol glycolate. Ester analysis as in Example 1 indicated that the ester was comprised of 78% monomeric ester and 22% polymeric esters. Hydrogenation was then performed using the catalyst of Example 1, a temperature of 360° F. and a pressure of 1,500 psig. Activity loss was found to be 0.37% per 100 hours.

EXAMPLE 8

This example was carried out essentially as Example 7. Analysis showed the product to contain 39% diethylene glycol glycolate, 13% of which was polymeric ester. Hydrogenation was conducted using the catalyst of Example 1, a temperature of 380° F. and a pressure of 340 psig. The loss in catalytic activity was 0.08% per 100 hours.

What is claimed is:

1. In the process of preparing ethylene glycol by hydrogenating a mixture comprising glycolic acid esters with more than 22% of the esters in the form of polyglycolide esters in the presence of a hydrogenation catalyst, the improvement of extending the life of said hydrogenation catalyst, which comprises heating said mixture to a temperature in about the range 300°–525° F., before hydrogenating it, with from 250 to 400 mol % excess of alcohol based on polyglycolide esters for a period of 20–90 minutes to transesterify said mixture and thereby lowering the polyglycolide ester content below about 22%, the aforesaid percentages being by weight based on the total ester content.

2. The improvement according to claim 1, wherein the hydrogenation catalyst is a copper-containing catalyst.

3. The improvement of claim 2, wherein in addition to copper the hydrogenation catalyst contains silica and zinc oxide.

4. The improvement according to claim 1, wherein the alcohol is ethylene glycol.

5. The improvement according to claim 1, wherein the alcohol is diethylene glycol.

* * * * *